(12) United States Patent
Amin

(10) Patent No.: US 12,274,454 B2
(45) Date of Patent: *Apr. 15, 2025

(54) SYSTEM AND METHOD FOR CREATING GRAFT TUNNELS IN BONE

(71) Applicant: Integrity Medical Services Inc., Yorba Linda, CA (US)

(72) Inventor: Nirav H. Amin, Yorba Linda, CA (US)

(73) Assignee: Integrity Medical Services Inc., Yorba Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/892,115

(22) Filed: Sep. 20, 2024

(65) Prior Publication Data

US 2025/0009365 A1    Jan. 9, 2025

Related U.S. Application Data

(63) Continuation of application No. 18/659,878, filed on May 9, 2024, now Pat. No. 12,102,338, which is a
(Continued)

(51) Int. Cl.
*A61B 17/16* (2006.01)
*A61B 17/00* (2006.01)
*A61B 90/00* (2016.01)

(52) U.S. Cl.
CPC ...... *A61B 17/1662* (2013.01); *A61B 17/1633* (2013.01); *A61B 90/03* (2016.02); *A61B 2017/0023* (2013.01); *A61B 2090/036* (2016.02)

(58) Field of Classification Search
CPC ............ A61B 17/1633; A61B 17/1675; A61B 17/1714; A61B 17/1764; A61B 2090/033; A61B 2090/036
See application file for complete search history.

(56) References Cited

U.S. PATENT DOCUMENTS

| 4,922,897 A | 5/1990 | Sapega et al. |
| 5,112,337 A | 5/1992 | Paulos et al. |

(Continued)

FOREIGN PATENT DOCUMENTS

| CN | 104083204 | 6/2016 |
| CN | 208081271 | 11/2018 |

(Continued)

OTHER PUBLICATIONS

Arthrex, FiberSnare® Suture. Undated; downloaded Jul. 17, 2024 from https://www.arthrex.com/knee/fibersnare; 4 pages.
(Continued)

*Primary Examiner* — Matthew J Lawson
(74) *Attorney, Agent, or Firm* — Knobbe Martens Olson and Bear, LLP

(57) ABSTRACT

Methods and devices for consistently and accurately controlling the depth of the graft tunnel. A sheath is inserted into the bone until a stop member on the sheath contacts the bone. A cutting member is then deployed to drill a larger bore in the tunnel until making contact with the distal end of the sheath. The cutting member may be drawn retrograde within the tunnel, or driven antegrade from an opening opposite the opening in which the sheath resides. The drill and the sheath can then be removed, leaving the tunnel that includes a tunnel portion sized to fit a graft so that the graft fits tightly within the tunnel portion and is flush with the opening of the tunnel.

14 Claims, 6 Drawing Sheets

Related U.S. Application Data continuation of application No. 18/438,310, filed on Feb. 9, 2024, now Pat. No. 12,023,049, which is a continuation of application No. 17/830,674, filed on Jun. 2, 2022, now Pat. No. 11,986,193, which is a continuation of application No. 16/858,070, filed on Apr. 24, 2020, now Pat. No. 11,357,517.

(60) Provisional application No. 62/838,575, filed on Apr. 25, 2019.

(56) References Cited

U.S. PATENT DOCUMENTS

| | | |
|---|---|---|
| 5,154,720 A | 10/1992 | Trott et al. |
| 5,163,940 A | 11/1992 | Bourque |
| 5,201,741 A | 4/1993 | Dulebohn |
| 5,330,468 A | 7/1994 | Burkhart |
| 5,374,269 A | 12/1994 | Rosenberg |
| 5,417,684 A | 5/1995 | Jackson et al. |
| 5,501,692 A | 3/1996 | Riza |
| 5,709,697 A | 1/1998 | Ratcliff et al. |
| 5,817,111 A | 10/1998 | Riza |
| 5,865,834 A | 2/1999 | McGuire |
| 5,895,389 A | 4/1999 | Schenk |
| 5,993,451 A | 11/1999 | Burkhart |
| 6,022,360 A | 2/2000 | Reimels et al. |
| 6,063,088 A | 5/2000 | Winslow |
| 6,120,511 A | 9/2000 | Chan |
| 6,254,605 B1 | 7/2001 | Howell |
| 6,676,668 B2 | 1/2004 | Mercereau et al. |
| 7,192,431 B2 | 3/2007 | Hangody et al. |
| 7,210,881 B2 | 5/2007 | Greenberg |
| 7,270,663 B2 | 9/2007 | Nakao |
| 7,575,578 B2 | 8/2009 | Wetzler et al. |
| 7,578,824 B2 | 8/2009 | Justin et al. |
| 7,771,483 B2 | 8/2010 | Justin et al. |
| 8,523,872 B2 | 9/2013 | Ek |
| 8,690,885 B2 | 4/2014 | Smith |
| 8,740,913 B2 | 6/2014 | Schneider |
| 8,888,795 B2 | 11/2014 | Chu |
| 9,023,056 B2 | 5/2015 | Berberich |
| 9,161,764 B2 | 10/2015 | Smith |
| 9,232,954 B2 | 1/2016 | Steiner et al. |
| 9,451,951 B2 | 9/2016 | Sullivan et al. |
| 10,098,646 B2 | 10/2018 | Ardito et al. |
| 10,492,804 B2 | 12/2019 | Amis et al. |
| 10,758,251 B2 | 9/2020 | Miller |
| 10,799,334 B2 | 10/2020 | Smigielski et al. |
| 10,888,349 B2 | 1/2021 | Pereira et al. |
| 11,033,283 B2 | 6/2021 | Mirochinik et al. |
| 11,166,732 B2 | 11/2021 | Maxon et al. |
| 11,202,641 B2 | 12/2021 | Biton et al. |
| 11,357,517 B1 | 6/2022 | Amin |
| 11,471,150 B2 | 10/2022 | Smith et al. |
| 11,504,140 B2 | 11/2022 | Fallin et al. |
| 11,903,602 B2 | 2/2024 | Sullivan et al. |
| 11,986,193 B2 | 5/2024 | Amin |
| 12,023,049 B2 | 7/2024 | Amin |
| 12,102,338 B2 | 10/2024 | Amin |
| 2002/0133165 A1 | 9/2002 | Whittaker et al. |
| 2004/0176771 A1 | 9/2004 | Schmieding |
| 2006/0173468 A1 | 8/2006 | Simmon et al. |
| 2006/0293689 A1 | 12/2006 | Miller et al. |
| 2007/0233128 A1 | 10/2007 | Schmieding |
| 2008/0154271 A1 | 6/2008 | Berberich et al. |
| 2008/0183174 A1 | 7/2008 | Sikora et al. |
| 2009/0171359 A1 | 7/2009 | Sterrett |
| 2011/0125156 A1 | 5/2011 | Sharkey |
| 2011/0166581 A1 | 7/2011 | Van Der Merwe et al. |
| 2011/0238074 A1 | 9/2011 | Ek |
| 2012/0109136 A1 | 5/2012 | Bourque et al. |
| 2014/0155899 A1 | 6/2014 | Bowman et al. |
| 2014/0276844 A1 | 9/2014 | Bourque et al. |
| 2014/0276884 A1 | 9/2014 | Lizardi et al. |
| 2015/0133941 A1 | 5/2015 | Saylor et al. |
| 2015/0190147 A1 | 7/2015 | Ferragamo et al. |
| 2015/0345927 A1 | 12/2015 | Bourque et al. |
| 2015/0351777 A1 | 12/2015 | Lizardi et al. |
| 2016/0089161 A1 | 3/2016 | Ardito et al. |
| 2017/0007279 A1 | 1/2017 | Sharma |
| 2017/0042556 A1 | 2/2017 | LaPrade et al. |
| 2017/0189036 A1 | 7/2017 | Rajeev |
| 2017/0245869 A1 | 8/2017 | Mirochinik |
| 2018/0153572 A1 | 6/2018 | Fojtik et al. |
| 2020/0375615 A1 | 12/2020 | Walker |
| 2022/0110640 A1 | 4/2022 | Kam et al. |
| 2022/0117720 A1 | 4/2022 | Ng et al. |
| 2023/0157808 A1 | 5/2023 | Cole et al. |
| 2025/0017605 A1 | 1/2025 | Amin |
| 2025/0017719 A1 | 1/2025 | Amin |

FOREIGN PATENT DOCUMENTS

| | | |
|---|---|---|
| CN | 217853139 U | 11/2022 |
| EP | 2419035 | 7/2017 |
| WO | WO 2018/075615 | 4/2018 |

OTHER PUBLICATIONS

DAIC—Diagnostic and Interventional Cardiology, SentreHeart Receives CE Mark for Lariat Suture Delivery Device. News Article; Oct. 28, 2015; downloaded from https://www.dicardiology.com/content/sentreheart-receives-ce-mark-lariat-suture-delivery-device; 1 page.

Espejo-Baena et al., Posterior Cruciate Ligament Reconstruction With Hamstring Tendons Using a Suspensory Device for Tibial Fixation and Interference Screw for Femoral Fixation. Arthroscopy Techniques. Feb. 1, 2017;6(1): e213-e218.

Yin et al., Transtibial Pull-Out Repair of Converted Radial Tear Adjacent to Medial Meniscus Root. Arthroscopy Techniques.Jan. 1, 2020;9(1): e171-e176.

Zimmer Biomet, SpeedSnare™ Surgical Suture Passer. Website for Healthcare Professionals; undated downloaded on Jul. 17, 2024 from https://www.zimmerbiomet.com/en/products-and-solutions/specialties/sports-medicine/speedsnare-surgical-suture-passer.html, 8 pages.

Petry A., SutureSnare™ Suture Passer—Product Demonstration; Anthrex Apr. 25, 2016, downloadedfrom https://www.arthrex.com/resources/VID1-00773-EN/suturesnare-suture-passer on Jul. 17, 2024; 4 pages.

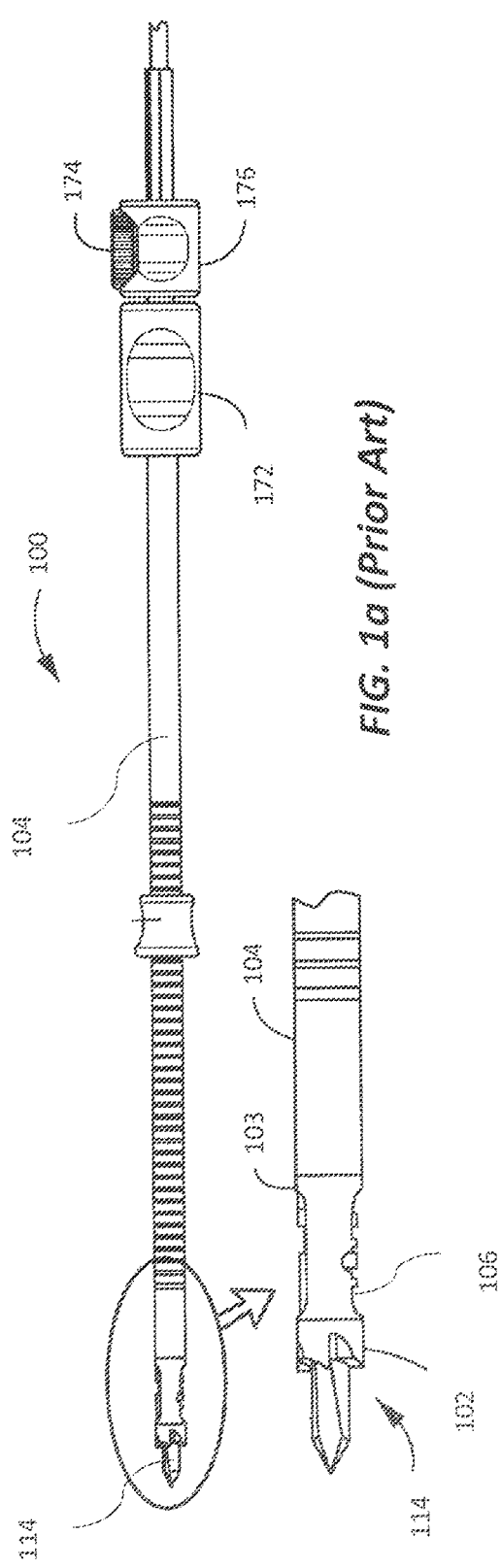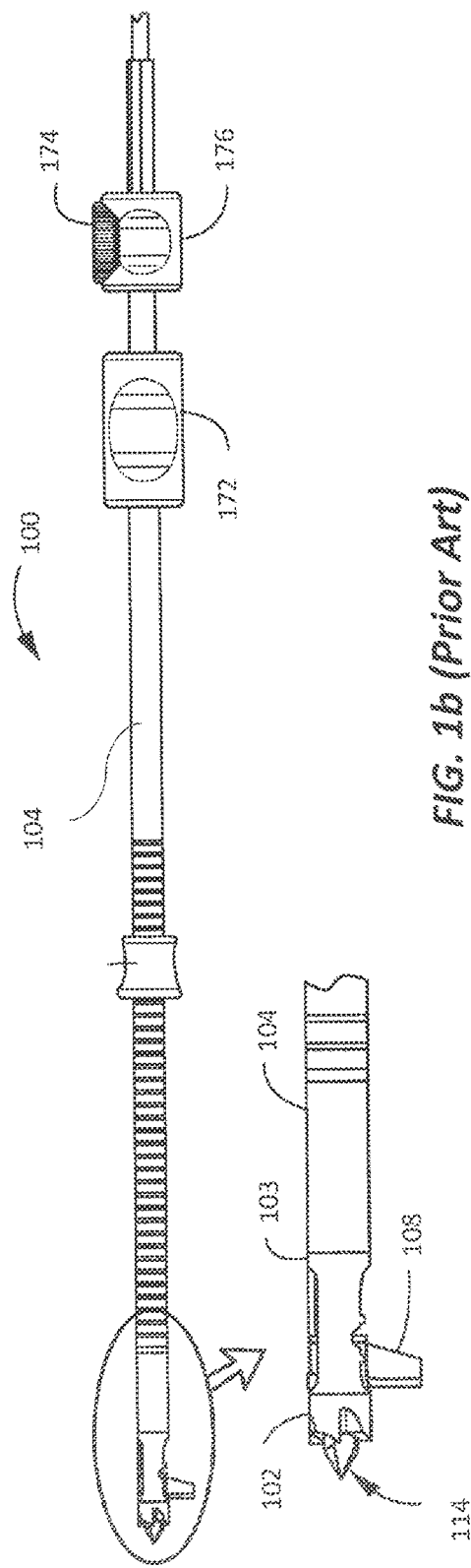
FIG. 1a (Prior Art)
FIG. 1b (Prior Art)

SYSTEM AND METHOD FOR CREATING GRAFT TUNNELS IN BONE

INCORPORATION BY REFERENCE TO ANY PRIORITY APPLICATIONS

This application is a continuation of U.S. application Ser. No. 18/659,878, filed May 9, 2024, which is a continuation of U.S. application Ser. No. 18/438,310, filed Feb. 9, 2024, which is a continuation of U.S. application Ser. No. 17/830,674, filed Jun. 2, 2022, which is a continuation of U.S. application Ser. No. 16/858,070, filed Apr. 24, 2020, now U.S. Pat. No. 11,357,517, which claims priority to U.S. Provisional Application 62/838,575, filed Apr. 25, 2019, which is hereby incorporated herein in its entirety.

TECHNICAL FIELD

The present disclosure relates to drill assemblies for creating tunnels through bone during arthroscopic ligament reconstruction surgery.

BACKGROUND

Desired outcomes for arthroscopic ligament reconstruction surgery are generally achieved by establishing the proper shape and placement of torn tissue. While performing such surgery, a surgeon typically makes a small incision in a patient's skin covering the surgical site (e.g., a bone joint) to allow a drill assembly to be placed in the bone joint to create tunnels through the patient's bone which are subsequently filled with a tissue graft, replicating the original damaged tissue. One such drill assembly, sometimes known as a retrograde reamer, can be configured to operate in both an antegrade (i.e., forward) drilling mode and a retrograde (i.e., reverse) cutting mode.

For a torn anterior cruciate ligament (ACL) reconstruction, for example, one approach to achieving proper placement of the tissue graft includes creating a tunnel in the patient's femur for insertion of the tissue graft. With this approach, a surgeon places a guidewire through the femur along an established path for creation of the bone tunnel. The surgeon then determines the size of a primary bone tunnel as well as the size of a counterbore through the bone appropriate to fit the replacement tendon graft. Once the proper size of the bone tunnel is established, the surgeon places the reamer with an appropriately sized drill bit over the guidewire to create the primary bone tunnel in an antegrade manner. The surgeon then retracts the guidewire and activates a mechanism to open or deploy a cutting member of the drill assembly within the bone joint. The surgeon then uses the cutting member to create a counterbore through the bone in a retrograde manner for insertion of the graft.

To avoid subsequent movement or elongation of the graft within the tunnel, it is important that the graft have a tight fit into the tunnel with a minimal distance between the end of the graft and the cortical surface of the bone. During the retrograde drilling, however, it can be difficult for a surgeon to safely and accurately assess the depth of the retrograde tunnel from outside of the joint. The surgeon must make an estimation of the depth of the tunnel by visualization as the drilling occurs, increasing the chances of a misfit between the tunnel and the tissue graft.

SUMMARY

The methods and devices described below provide for consistent and accurate control of the depth of the tunnel created to accommodate a graft during ACL repair. The drill system includes a drill assembly and a sheath having a depth stop on an outer surface of the sheath. The sheath is slidable over the shaft of the drill and partially insertable into the bone tunnel. To prepare the bone tunnel for receipt of the tissue graft, the total length of the antegrade tunnel is first measured. The graft length is known from its preparation step and is equal to the desired length of the retrograde tunnel. A depth stop length can thus be calculated by subtracting the graft length from the total tunnel length. The sheath is inserted over the drill into the antegrade tunnel until the stop member on the sheath contacts the bone. When this happens, the length of the sheath portion inserted into the tunnel is equal to the depth stop length. The cutting member is then deployed to begin retrograde drilling until making contact with the distal end of the sheath. The drill and the sheath can then be removed, leaving the tunnel created for the proper graft length.

Examples of the drill assembly and method of this disclosure may include one or more of the following, in any suitable combination.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

FIGS. 1a and 1b depict an example of a prior art drill assembly.

DETAILED DESCRIPTION OF THE PREFERRED EMBODIMENT

Figure 2A:
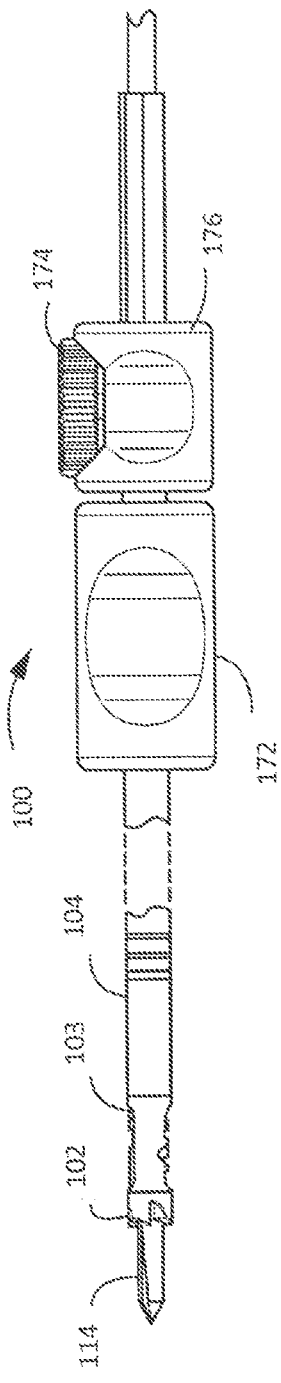
FIGS. 2a through 2c illustrate the use of the drill assembly of FIGS. 1a and 1b.

FIGS. 1a and 1b show an example of prior art drill assembly 100 for securing a tissue to bone. FIG. 1a depicts a side view of the drill assembly 100, as well as a detailed view of a drill bit 102 having a tubular (cannulated) inner shaft 103 disposed over a guidewire 114. FIG. 1b depicts a further side view of the drill assembly 100, as well as a detailed view of the drill bit 102 and the cutting member 108 in its fully-opened or deployed position. As shown in FIGS. 1a and 1b, the inner shaft 103 extends through an outer shaft 104 with the cutting member 108 being operatively coupled within an opening or cavity 106 near a distal end of the inner shaft 103. The inner shaft 103 is coupled to a mechanism including, for example, a slide actuator 172, a lock knob 174 and a plunger support 176 for manually opening or deploying the cutting member 108, as further described below. The cutting member 108 can further include at least one through hole (not shown) allowing for the passage of the guidewire 114 through the cutting member 108 in its closed and/or open positions.

Figure 2B:
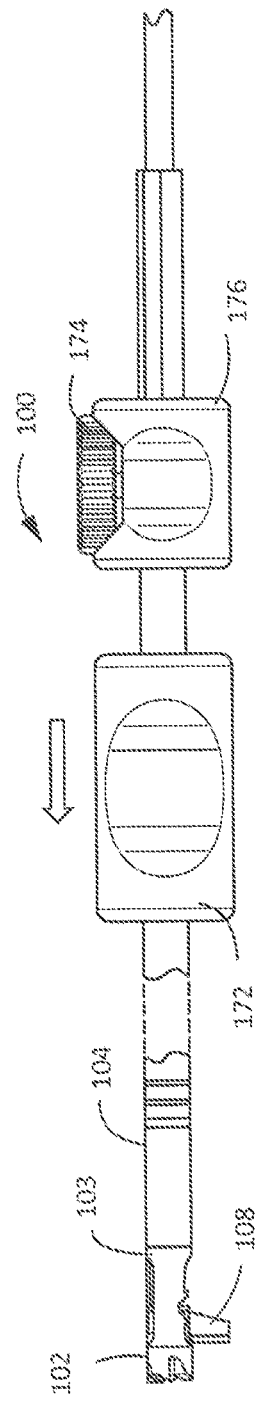
Figure 2C:
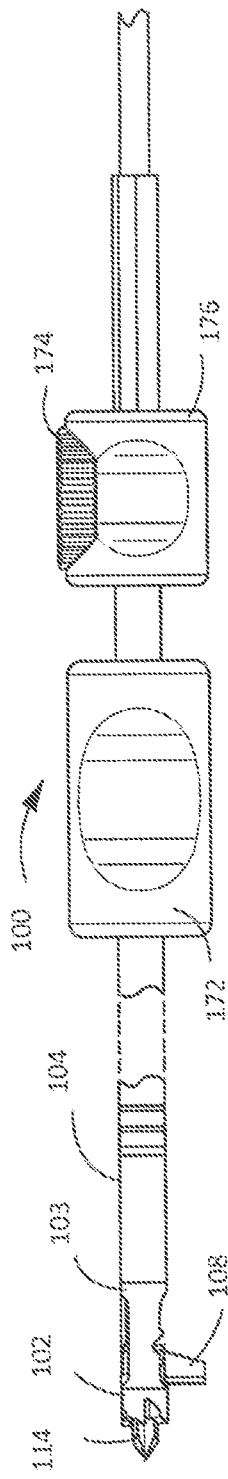

FIGS. 2a through 2c depict the deployment of the drill assembly 100 of FIGS. 1a and 1b. As shown in FIG. 2a, the inner shaft 103 is configured to be disposed over the guidewire 114. As shown in FIG. 2b, once the guidewire 114 is at least partially retracted within the inner shaft 103, the slide actuator 172 can be moved along the inner shaft 103 toward the distal end of the inner shaft 103 in a single manual motion to move the cutting member 108 to its deployed position. As shown in FIG. 2c, once the cutting member 108 is in its fully-deployed position, the lock knob 174 can be rotated to secure, stabilize, and strengthen the guidewire 114, the inner shaft 103, and the cutting member 108 as a unit. To move the cutting member 108 from its opened or deployed position back to its closed position, the surgeon can move the slide actuator 172 along the inner shaft 103 toward the proximal end of the inner shaft 103, thereby closing the cutting member 108.

Having described the above example of a drill assembly 100, it should be noted that the drill assembly of this disclosure can take the form of any drill assembly in which consistent and accurate control of the depth of the retrograde tunnel is needed. Non-limiting examples of suitable drill assemblies are further described in U.S. Publication No. 2014/0276844 to Smith & Nephew, Inc. (Memphis, TN), incorporated herein by reference.

Figure 3A:
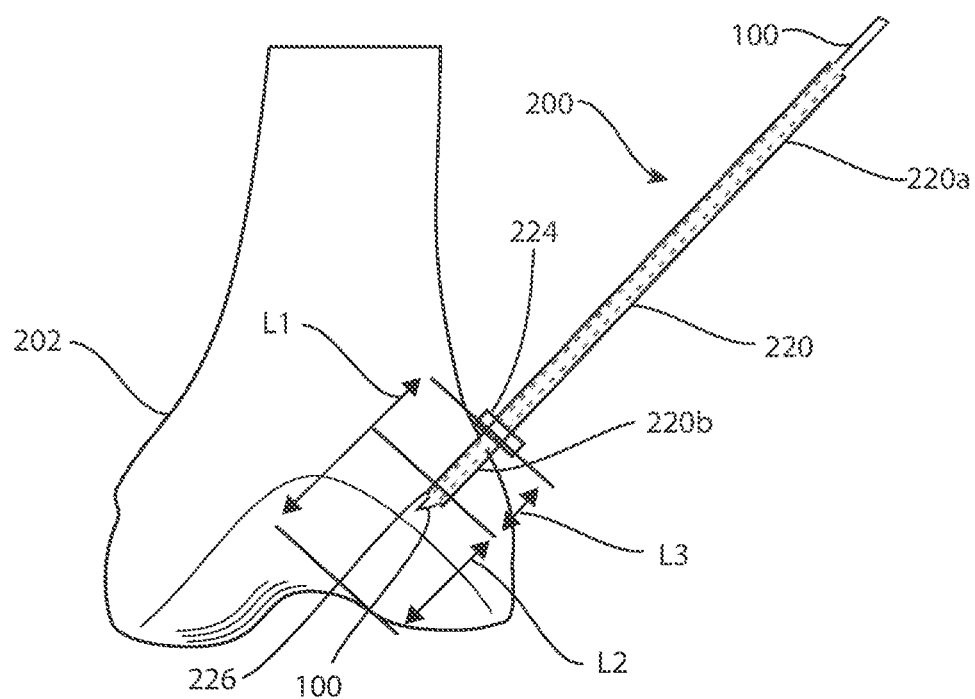
FIG. 3a illustrates an example of a drill assembly of this disclosure.

Turning now to FIG. 3a, an example of the drill assembly 200 of this disclosure is shown inserted into a bone 202. In the example shown in FIG. 3a, the bone 202 is a femur, however other bones may be machined in a similar manner to support other types of repair. The drill assembly 200 is substantially similar to the drill assembly 100 shown in FIGS. 1a and 1b, except as described below. The drill assembly 200 is shown disposed within a sheath 220 configured to slide over the outer shaft (item 104 in FIGS. 1a through 2c). The sheath 220 includes a stop member 224 extending radially from a surface of the sheath 220. The stop member 224 is fixed to the sheath 220 proximal to a distal end 226 of the sheath 220. In the example shown in FIG. 3, the stop member 224 extends around the entire circumference of the sheath 220. However the stop member 224 could extend for less than the entire circumference of the sheath 220, and the stop member could slidable along the sheath, to a desired position, and fixed with the set screw or other mechanism, during the procedure. The diameter of the sheath 220 may decrease in size from a first portion 220a of the sheath extending proximally from the stop member 224 to a second portion 220b of the sheath 220 extending distally from the stop member 224. For example, a diameter of the first portion 220a may be about 4.0 mm and a diameter of the second portion 220b may be about 3.5 mm. The sheath may be disposable or reusable.

Still referring to FIG. 3a, to begin the repair, a total tunnel length $L^1$ of a bone tunnel through the bone 202 to be drilled is determined. For example, the guidewire 114 (FIGS. 2a through 2c) is inserted into the bone 202 and the total tunnel length $L^1$ is measured with a depth gauge (not shown) calibrated to the guide wire 114. The guidewire may be a 2.4 mm guidewire, or any other suitable guidewire or guide pin designed to provide more accurate bone tunnel placement during arthroscopic ligament reconstruction surgery. A length of the bone graft (not shown) is determined during the preparation of the bone graft and corresponds to a desired length $L^2$ of the retrograde tunnel. Thus, a retrograde depth stop length $L^3$ can be determined by subtracting the retrograde tunnel length $L^2$ from the total tunnel length $L^1$.

The length of the second portion 220b of the sheath 220 is selected such that, when the sheath 220 is placed over the outer shaft (item 104 in FIGS. 1a through 2c), a distance between the stop member 224 and a distal end 226 of the sheath 220 is equal to the depth stop length $L^3$. Several sheaths having second portions of varying lengths may be provided, and a surgeon may select the best fit depending on the measured total length $L^1$. For example, if the total length $L^1$ of the bone 202 is 37 mm and a desired length of the retrograde tunnel $L^2$ is 25 mm, then a sheath 220 having a depth stop length $L^3$ of either 10 mm or 12.5 mm could be used. In another example, if the total length $L^1$ of the bone 202 is 35 mm and a desired length of the retrograde tunnel $L^2$ is 20 mm, then a sheath 220 having a depth stop length $L^3$ of 15 mm could be used. In yet another example, if the total length $L^1$ of the bone 202 is 38 mm and a desired length of the retrograde tunnel $L^2$ is 25.5 mm, then a sheath 220 having a depth stop length $L^3$ of 12.5 mm could be used. Alternatively, a single sheath may be provided, and the surgeon may cut the sheath to length after measuring the total length $L^1$.

Figure 3B:
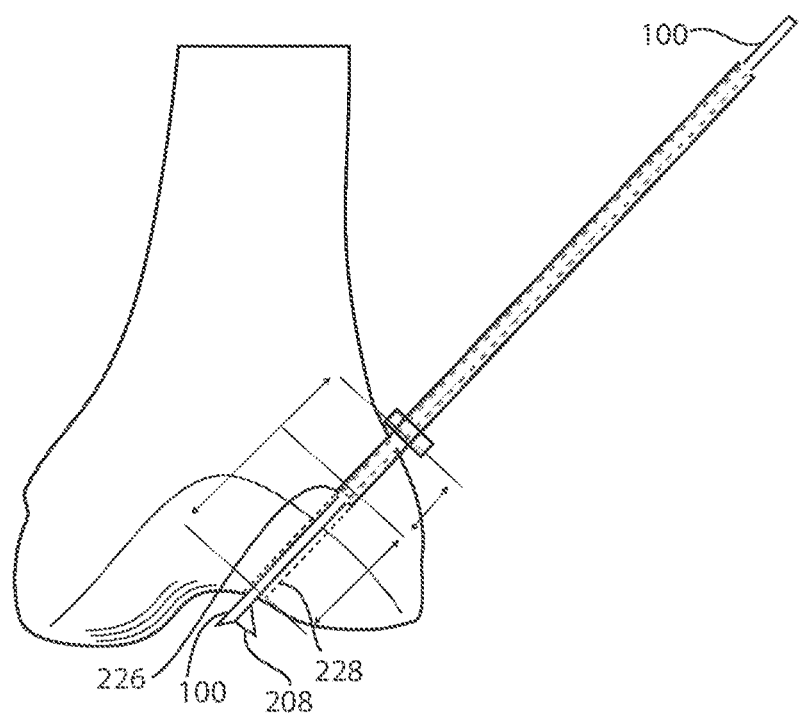
FIGS. 3b through 3d depict a use of the drill assembly of FIG. 3a during an ACL repair.
Figure 3C:
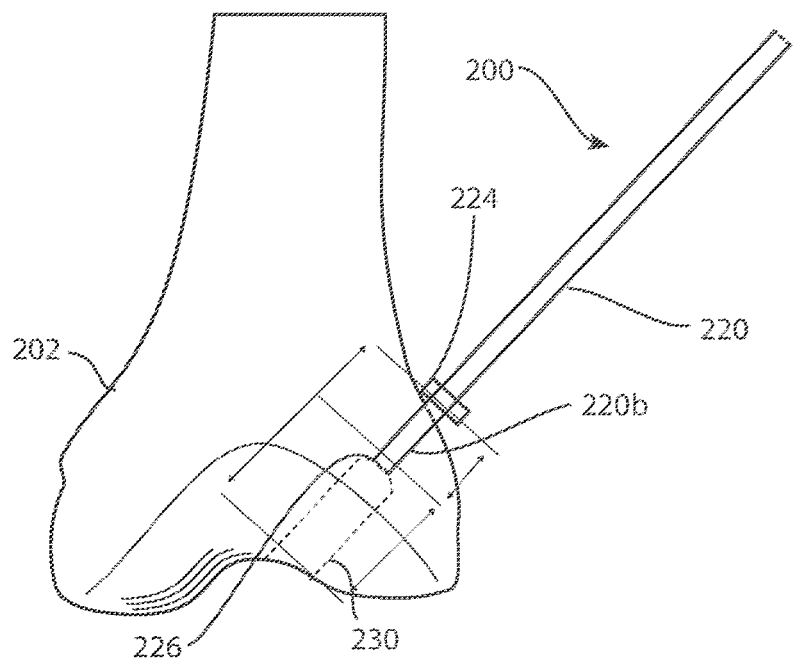
Figure 3D:
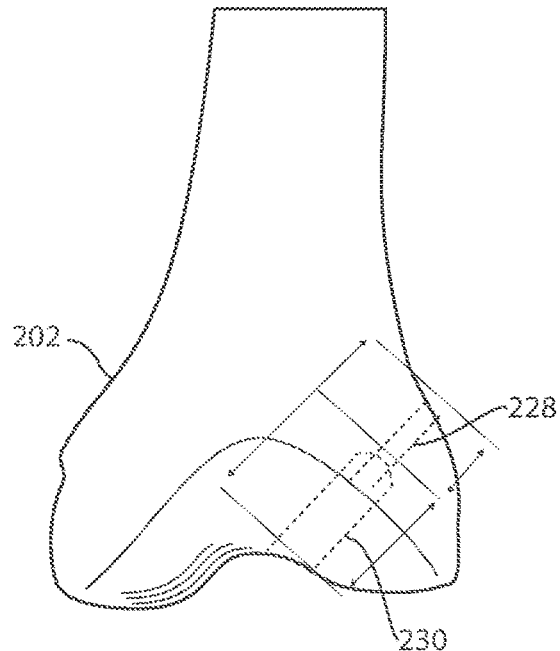

As shown in FIG. 3b, the assembled drill assembly 100 and sheath 220 comprise a system (item 200) which may be used to initially drill an antegrade tunnel 228 having the length $L^1$ through the bone 202. (The "antegrade" tunnel is the tunnel formed by moving the drill forward into the bone, using the drill bit 102.) The sheath 220 is then inserted into the antegrade tunnel until the stop member meets the cortex of the bone. The cutting member 208 is then deployed to begin the retrograde drilling. The drill assembly is pulled back out of the antegrade tunnel while rotating, with the cutting member deployed, while leaving the sheath in place as shown, so that the cutting member 208 (item 108 in FIGS. 1a and 1b) drills in a retrograde manner, creating the retrograde tunnel 230 (FIG. 3c), until the cutting member 208 reaches the distal end 226 of the sheath 220. The distal end 226 of the sheath 220 prevents further movement of the cutting member 208, which prevents further retrograde drilling by the cutting member 208. The cutting member 208 is then moved to the closed position and the drill assembly and sheath system 200 can be removed from the bone 202, leaving the retrograde tunnel 230 created for the proper graft length (FIG. 3d). The resultant retrograde tunnel 230 has a larger bore than the remaining portion of the antegrade tunnel.

The drill assembly, sheath and stop are thus useful in a method of creating a tunnel through bone with a first portion of the tunnel having a first diameter, and a second portion of the tunnel having a second diameter larger than the first diameter, by inserting the tip of a drilling assembly into the bone and drilling into the bone in a first direction using a first cutting element of a first diameter to drill entirely through the bone, inserting the sheath over the drill assembly and into the first tunnel until a distal end of the sheath is disposed at a predetermined depth in the tunnel, and thereafter deploying a second cutting element of a second diameter and withdrawing the tip of the drilling assembly while operating the second cutting element to create the second portion of the tunnel, and ceasing operation of the second cutting element when the second cutting element meets the distal end of the sheath. The predetermined depth may be chosen by determining the total length of the tunnel and the desired length of the second portion of the tunnel, and inserting the sheath into the tunnel to a depth corresponding to the difference between the two. A stop member may be fixed to the outside of the sheath, at a distance from the distal end of the sheath corresponding to the predetermined depth of the first tunnel, or correspondingly, the desired length of the second portion of the tunnel.

Depending on the desired depth stop length $L^3$, a plurality of sheaths 220 having different depth stop lengths $L^3$ could be used with the drill assembly 100 of this disclosure. Thus a kit of this disclosure may include the drill assembly 100 of this disclosure including a plurality of sheaths 220 having different depth stop lengths $L^3$. In a non-limiting example, the kit may include a sheath 220 having a depth stop length $L^3$ of 10 mm, a sheath 220 having a depth stop length $L^3$ of 12.5 mm and a sheath 220 having a depth stop length $L^3$ of 15 mm. The stops may be formed as flanges on the sheath. Alternatively, a single sheath may be provided and the stop may comprise a collar which is translatable along the outside of the sheath, and the stop may be provided with a set screw or other means for fixing it longitudinally to the sheath. The sheath 220 could be used with tunnel-creating instruments which are pounded or screwed, rather than drilled, into the bone 202, in which case pins may be used as tunnel creating means in lieu of or in addition to the drill assembly.

Figure 4A:
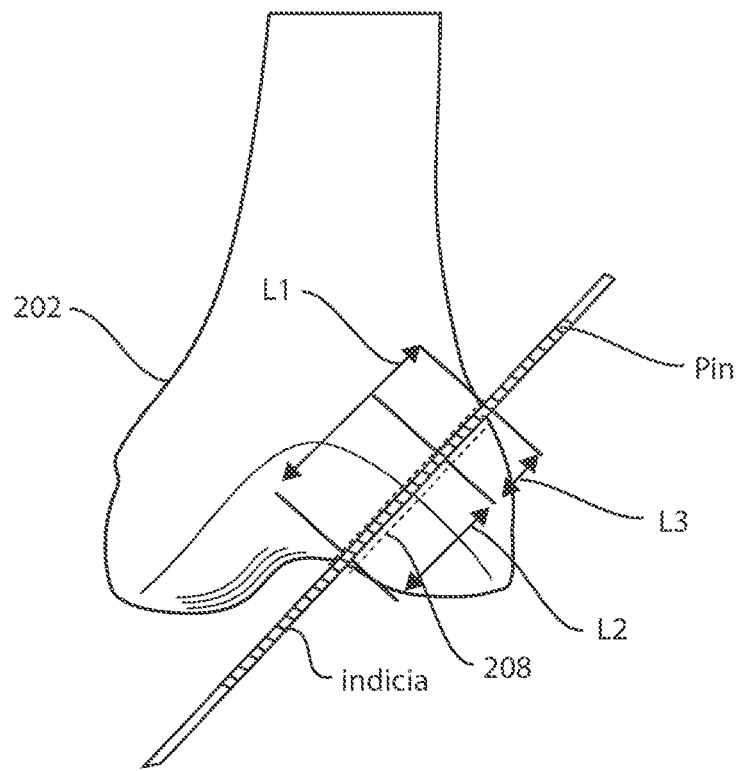
FIGS. 4a through 4d depict use of the drill assembly and a collared sheath during an ACL repair.
Figure 4B:
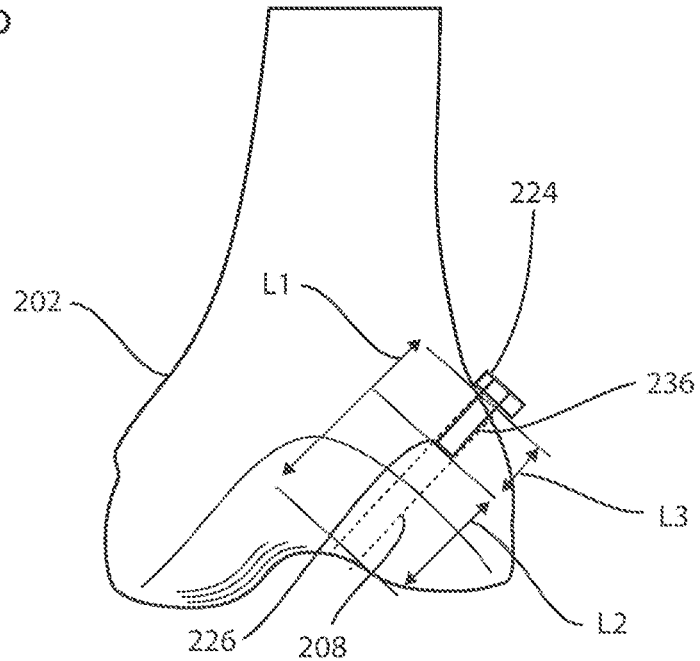
Figure 4C:
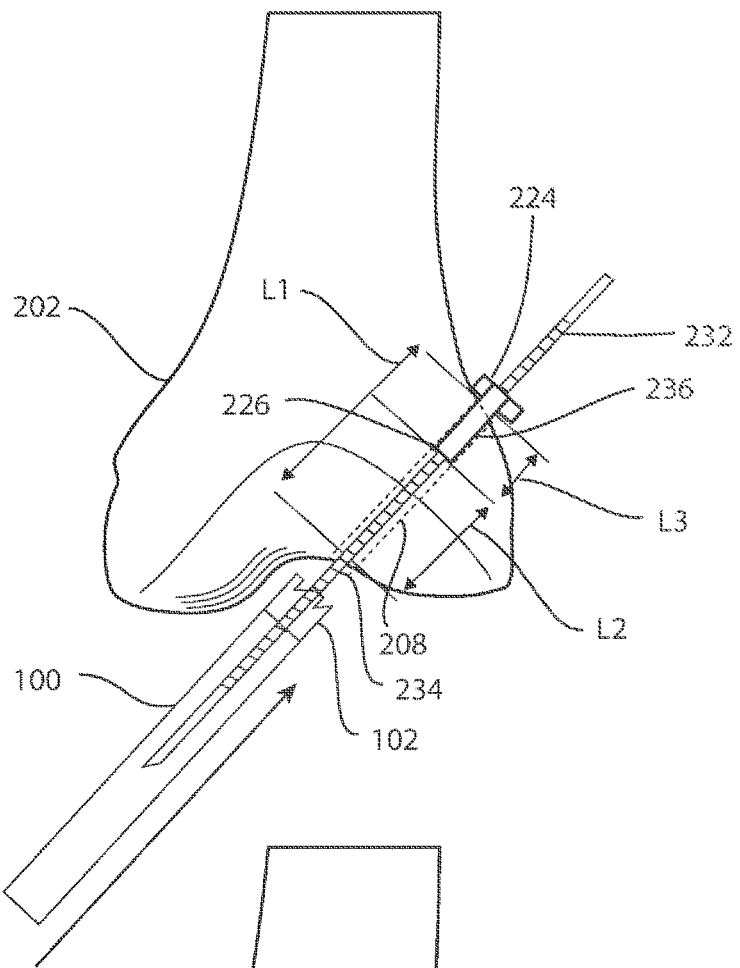
Figure 4D:
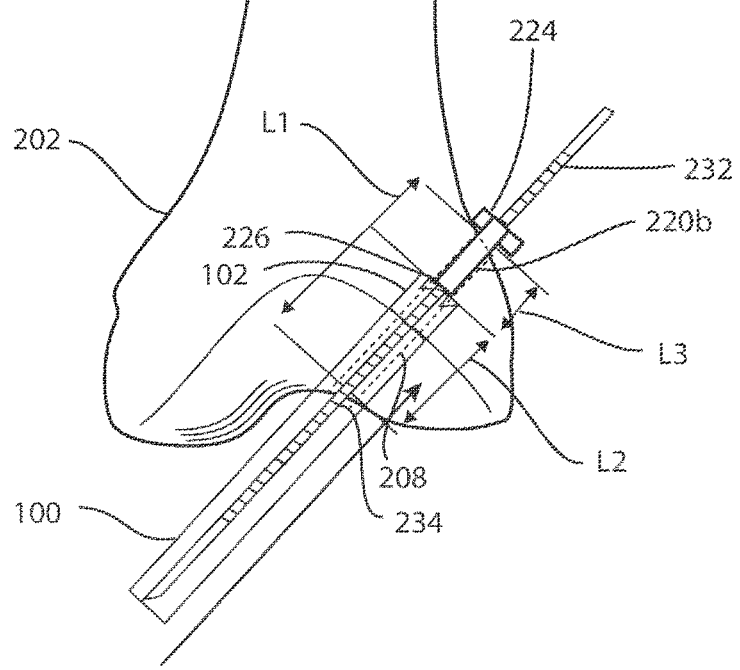

FIGS. 4a through 4d illustrate another method in which a sheath may be placed in a tunnel to limit the penetration of a drill or reamer in order to control the extent of a second portion of the tunnel (the graft portion of the tunnel). As shown in FIG. 4a, to create the tunnel 228 initially, the tunnel 208 is created, drilling from inside the joint, with a drill bit entering the bone at the intra-articular lateral cortex and drilling through the medial condyle and exiting the condyle at a medial opening, or vice-versa. The length of the tunnel 228 is then measured with a ruled pin 232. The ruled pin is marked with indicia 234 like a ruler, indicating length along the pin. As shown in FIG. 4a, the surgeon inserts the ruled pin 232 into the tunnel 228, and marks or notes the indicia proximate the entry point and exit point (on the intra-articular lateral cortex opening and the medial opening) to determine the length of the tunnel 228. Depending on the desired length of the first portion of the tunnel (to be used to pass sutures and pull graft material into the tunnel) and/or the desired length second portion of the tunnel (to be used to accommodate and integrate with the graft material), the surgeon chooses a sheath 236 with a length to match the desired length of the first portion/and or the second portion, or trims a sheath to fit. The sheath 236 is similar to the sheath 220b, and comprises the stop member 224 which may be configured as a flange or collar on the proximal end of the sheath 236. For this method, the sheath terminates proximally at the stop member, and does not include a proximal portion corresponding to 220a of FIG. 3. As shown in FIG. 4b, the surgeon inserts the sheath 236, over the pin if appropriate, into the tunnel 228 until the stop 224 meets the bone of the medial condyle. With the sheath in place, with the distal end 226 of the sheath located within the bone at a point corresponding to the desired length of the second portion of the tunnel, the surgeon will insert a drill or reamer 100 over the pin, or otherwise into the tunnel, as shown in FIG. 4C and will drill or ream the tunnel to create the larger bore second portion, inserting the drill or reamer until the distal tip of the drill bit 102 of the reamer impinges on the sheath distal end 226 and is impeded from further insertion by the sheath, as shown in FIG. 4d. (In accordance with current terminology pertaining to medical devices, the proximal direction will be that direction on the device that is furthest from the patient and closest to the user, while the distal direction is that direction closest to the patient and furthest from the user, typically corresponding to the direction of insertion into the patient. These directions are applied along the longitudinal axis of the minimally invasive medical devices such as drills and sheaths, which is generally an axially elongate structure.) The result is a tunnel as previously shown in FIG. 3d with a first 1 small bore portion 208 located medially on the bone, and a second, larger bore portion 230, opening to the intra-articular lateral cortex of the condyle.

The method of FIGS. 4a through 4d for creating a tunnel for ACL repair may be generalized for use in other joints and bones, to create a tunnel through bone with a first portion of the tunnel having a first diameter, and a second portion of the tunnel having a second diameter larger than the first diameter, by creating a tunnel in the bone, with the tunnel communicating through the bone from a first location and to a second location; providing a sheath, wherein the sheath is characterized by a distal end and a proximal end, and comprises a stop member on the proximal end of the sheath, and the length of the sheath extending distally from the stop member has a length matching a desired length of the first portion of the tunnel; inserting the sheath into one of the first and second locations until the stop meets the exterior of the bone, locating the distal end of the sheath within the bone at a point corresponding to the desired length of the second portion of the tunnel; inserting a drill or reamer into the tunnel at the other of the first and second locations, and operating the drill or reamer to create the larger diameter second portion, until the distal tip of a drill bit of the drill or reamer impinges on the sheath distal end and is impeded from further insertion by the sheath.

While the devices and methods described above have been illustrated in the context of ACL repair and orthopedic surgery of the knee, they may be used in other procedures that require tunnels to accommodate tissue grafts and other implants. While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

What is claimed is:

1. A system for creating a tunnel through tissue, said system comprising:
    a drill assembly comprising:
        a shaft having a proximal end and distal end, the distal end of the shaft configured to form a first tunnel through a tissue; and
        a cutting member configured to move between a closed position and a deployed position to form a second tunnel through the tissue; and
        a sheath slidably disposed over the shaft, the sheath including a stop member extending radially from an outer surface of the sheath, the sheath configured to slide into the first tunnel such that the stop member contacts a surface of the tissue.

2. The system of claim 1, wherein a diameter of a first portion of the sheath extending proximally from the stop member is selected to be greater than a diameter of a second portion of the sheath extending distally from the stop member.

3. The system of claim 2, wherein the diameter of the first portion of the sheath is about 4.0 mm and the diameter of the second portion of the sheath is about 3.5 mm.

4. The system of claim 2, wherein a length of the second portion of the sheath is between 10 mm and 15 mm.

5. The system of claim 2, wherein a length of the second portion of the sheath is selected to be equal to a length of the second tunnel.

6. The system of claim 1, wherein the stop member extends around an entire circumference of the sheath.

7. The system of claim 1, wherein the sheath is disposable.

8. A kit comprising:
   a drill comprising:
   a shaft having a proximal end and distal end, the distal end of the shaft configured to form a first tunnel through a tissue; and
   a cutting member configured to move between a closed position and a deployed position to form a second tunnel through the tissue; and
   a plurality of sheaths configured to be slidable over the shaft, each of the plurality of sheaths including a stop member extending radially from a surface of the sheath, the sheath configured to slide into the first tunnel such that the stop member contacts a surface of the tissue.

9. The kit of claim 8, wherein a diameter of a first portion of each of the plurality of sheaths extending proximally from the stop member is selected to be greater than a diameter of a second portion extending distally from the stop member.

10. The kit of claim 9, wherein the diameter of the first portion of each of the plurality of sheaths is about 4.0 mm and the diameter of the second portion is about 3.5 mm.

11. The kit of claim 9, wherein a length of the second portion of each of the plurality of sheaths is between 10 mm and 15 mm.

12. The kit of claim 9, wherein a length of the second portion is selected to be equal to a length of the second tunnel.

13. The kit of claim 8, wherein the stop member extends around an entire circumference of each of the plurality of sheaths.

14. The kit of claim 8, wherein each of the plurality of sheaths is disposable.

* * * * *